United States Patent
Xing et al.

(10) Patent No.: US 12,058,988 B2
(45) Date of Patent: Aug. 13, 2024

(54) WARM WATER IMMERSION-BASED HATCHING METHOD OF SILKWORM EGGS

(71) Applicant: Sericulture and Agri-Food Research Institute, Guangdong Academy of Agricultural Sciences, Guangzhou (CN)

(72) Inventors: Dongxu Xing, Guangzhou (CN); Qiong Yang, Guangzhou (CN); Sentai Liao, Guangzhou (CN); Yang Xiao, Guangzhou (CN); Qingrong Li, Guangzhou (CN)

(73) Assignee: SERICULTURE AND AGRI-FOOD RESEARCH INSTITUTE, GUANGDONG ACADEMY OF AGRICULTURAL SCIENCES, Guangzhou (CN)

( * ) Notice: Subject to any disclaimer, the term of this patent is extended or adjusted under 35 U.S.C. 154(b) by 163 days.

(21) Appl. No.: 17/742,433

(22) Filed: May 12, 2022

(65) Prior Publication Data
US 2023/0200364 A1 Jun. 29, 2023

(30) Foreign Application Priority Data
Dec. 29, 2021 (CN) ......................... 202111645418.4

(51) Int. Cl.
*A01K 67/04* (2006.01)
(52) U.S. Cl.
CPC .................................... *A01K 67/04* (2013.01)
(58) Field of Classification Search
CPC ...... A01K 67/04; A01K 61/17; A01K 67/033; A01K 67/0332; A01K 67/0335

USPC ............................................ 119/270, 6.6, 6.7
See application file for complete search history.

(56) References Cited

U.S. PATENT DOCUMENTS

| | | | | |
|---|---|---|---|---|
| 5,932,237 | A * | 8/1999 | Raulston | A01N 63/12 424/405 |
| 7,789,039 | B2* | 9/2010 | Hance | A01N 25/34 119/6.5 |
| 2021/0138071 | A1* | 5/2021 | Santos | C07K 16/22 |

FOREIGN PATENT DOCUMENTS

| | | | | |
|---|---|---|---|---|
| CN | 107494420 | A * | 12/2017 | A01K 67/02 |
| CN | 108235971 | A * | 7/2018 | A01K 67/04 |
| CN | 107812213 | B * | 7/2020 | A01K 67/04 |
| WO | WO-2018233341 | A1 * | 12/2018 | A01K 67/04 |

OTHER PUBLICATIONS

CN-107812213-B_MACHINE Translation (Year: 2020).*

(Continued)

*Primary Examiner* — David J Parsley
*Assistant Examiner* — Sahar Almatrahi
(74) *Attorney, Agent, or Firm* — Gearhart Law, LLC

(57) ABSTRACT

The present disclosure provides a warm water immersion-based hatching method of silkworm eggs, belonging to the technical field of sericulture production. In the present disclosure, a warm water treatment is conducted on silkworm eggs of a bivoltine silkworm variety in production, and a water temperature and an immersion time are optimized to ensure a higher hatching rate. The silkworm eggs are subjected to the warm water immersion at 49° C. to 51° C. for 15 s to 23 s to rapidly hatch the silkworm eggs without diapause.

15 Claims, 2 Drawing Sheets

(56) References Cited

OTHER PUBLICATIONS

WO-2018233341-A1_MACHINE Translation (Year: 2018).*
CN-107494420-A_MACHINE Translation (Year: 2017).*
CN-108235971-A_MACHINE Translation (Year: 2018).*

* cited by examiner ized Chinese Patent Application No. 202111645418.4, entitled
WARM WATER IMMERSION-BASED HATCHING METHOD OF SILKWORM EGGS

CROSS REFERENCE TO RELATED APPLICATION

This patent application claims the benefit and priority of Chinese Patent Application No. 202111645418.4, entitled "WARM WATER IMMERSION-BASED HATCHING METHOD OF SILKWORM EGGS" filed on Dec. 29, 2021, the disclosure of which is incorporated by reference herein in its entirety as part of the present application.

TECHNICAL FIELD

The present disclosure belongs to the technical field of sericulture production, and in particular relates to a warm water immersion-based hatching method of silkworm eggs.

BACKGROUND ART

Sericulture is an agricultural advantage and characteristic industry in China. The *Bombyx mori* is one member of the holometabolous class of insects, which possesses four distinguished developmental stages, i.e., egg, larva, pupa, and adult (moth). Under natural conditions, silkworm eggs gradually enter a diapause state after being laid from moth body, and the diapause state can only be released after a period of low-temperature protection. Since 19th century, people have tried various hatching methods, including a friction hatching method, an air pressure hatching method, an induction hatching method, an ultraviolet hatching method, an oxygen hatching method, a hydrochloric acid hatching method and a sulfuric acid hatching method, hoping to artificially stimulate silkworm eggs with physical or chemical stimulations to hatch as soon as possible, thereby achieving multiple breeding of silkworms within a year. Among above methods, the hydrochloric acid hatching method has been used up to now with a best effect. The hydrochloric acid hatching method has high hatching rate, uniform hatching, and no damage to embryo physiology in eggs; meanwhile, it can supply silkworm eggs at any time according to needs of production.

However, the hydrochloric acid hatching method also has great disadvantages, such as higher cost and stricter processing requirements. Moreover, hydrochloric acid will pollute environment, be highly irritating and toxic to operators, and be highly corrosive to mechanical facilities. In addition, with increasingly strict control of chemicals by country, purchase and management of hydrochloric acid are becoming increasingly troublesome. In recent years, novel methods have also been explored. For example, Yamamoto et al. found that although dimethyl sulfoxide (DMSO) and some alkane reagents could also block silkworm eggs from entering diapause to varying degrees, but effect of preventing diapause was only 78%; Manqiao Jiang et al. treated silkworm eggs 20 h after oviposition with different acids and warm water. Results showed that the silkworm eggs had a hatching rate reaching not less than 95% after 15% nitric acid treatment; while treatments with 15% phosphoric acid and 15% acetic acid could promote hatching of silkworm eggs, with a relatively low hatching rate, and a gradual increase of immersion concentration resulted in a continuously-improved hatching effect of silkworm eggs. Scholars at home and abroad generally believe that acid immersion to release diapause of silkworm eggs is mainly due to changes of a pH value inside and outside silkworm eggs caused by $H^+$, thereby leading to changes of an enzyme activity in silkworm eggs.

SUMMARY

In view of this, an objective of the present disclosure is to provide a warm water immersion-based hatching method of silkworm eggs. A rapid treatment of silkworm eggs with an aqueous solution of a specific temperature can achieve a higher hatching rate.

The present disclosure provides a warm water immersion-based hatching method of silkworm eggs, including following steps:

subjecting silkworm eggs to warm water immersion at 48° C. to 51° C. for 15 s to 23 s.

Preferably, the warm water include 0.1 g/L to 0.3 g/L of chitosan, 0.01 g/L to 0.2 g/L of hydroxypropyl cellulose and 0.05 g/L to 0.2 g/L of γ-aminobutyric acid.

Preferably, the warm water include 0.15 g/L to 0.25 g/L of the chitosan, 0.05 g/L to 0.15 g/L of the hydroxypropyl cellulose and 0.1 g/L to 0.15 g/L of the γ-aminobutyric acid.

Preferably, a temperature of the warm water immersion is 50.5° C., and a time of the warm water immersion is 15 sec.

Preferably, an egg age of the silkworm eggs is 17 h to 21 h.

Preferably, an egg age of the silkworm eggs is 18 h.

Preferably, before immersion, a culture temperature of the silkworm eggs is 24° C. to 26° C. and a culture humidity is 75% to 85%.

Preferably, the silkworm eggs are derived from one or more varieties selected from a group consisting of 9 Fu, 7 Xiang, Liangguang 2, Yuecan 6 and Yuecan 8.

Preferably, the silkworm eggs are subjected to air-drying, incubation and hatching successively after warm water immersion.

Preferably, the air-drying is conducted for 20 min to 30 min.

Preferably, the incubation of silkworm eggs or the hatching is conducted at 26° C. to 28° C. and a relative humidity of 80% to 85%.

In a hatching method of silkworm eggs herein, a warm water treatment is conducted on silkworm eggs of a bivoltine silkworm variety in production, and a water temperature and an immersion time are optimized to ensure a higher hatching rate. The silkworm eggs are subjected to a warm water immersion at 48° C. to 51° C. for 15 s to 23 s to rapidly hatch the silkworm eggs without diapause. Method herein has a practical hatching rate reaching not less than 98%, with no adverse effect on a quality of silkworm cocoons, thereby achieving a same hatching effect as a hydrochloric acid hatching method. Compared with the hydrochloric acid hatching method, the method provided by the present disclosure has low cost, simple operation, no need of hydrochloric acid, and goes green with no adverse effect on human beings and environment. Thus, the method has a wide application prospects.

Meanwhile, the method can also effectively inactivate *Nosema bombycis* in poisonous silkworm eggs to effectively block egg transmission of silkworm pebrine disease.

Further, warm water includes 0.1 g/L to 0.3 g/L of chitosan, 0.01 g/L to 0.2 g/L of hydroxypropyl cellulose and 0.05 g/L to 0.2 g/L of γ-aminobutyric acid. Certain auxiliary materials are added to warm water to improve a heat resistance of silkworm embryos, thus further improving the practical hatching rate.

DETAILED DESCRIPTION OF THE EMBODIMENTS

Figure 1:
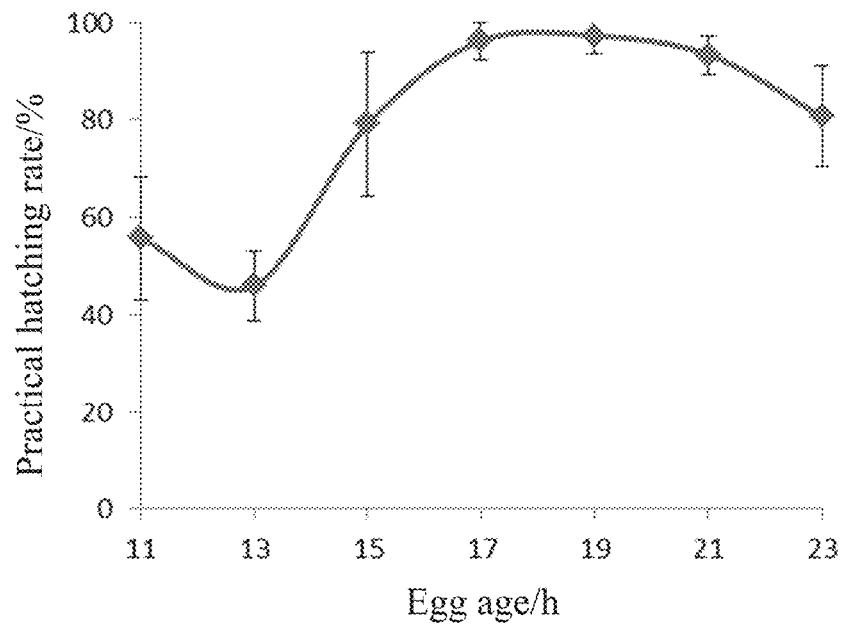
FIG. 1 shows an effect of an egg age on hatching rate of silkworm eggs of "Liangguang 2"

The present disclosure provides a warm water immersion-based hatching method of silkworm eggs, including following steps:

subjecting the silkworm eggs to warm water immersion at 48° C. to 51° C. for 15 s to 23 s.

In the present disclosure, a temperature of the warm water immersion is preferably 49° C. to 50.5° C., most preferably 50.5° C.; a time of the warm water immersion is preferably 15 s to 20 s, most preferably 15 s. Compared with warm water immersion-based hatching methods in the prior art, the method of the present disclosure reduces a water temperature and prolongs an immersion time, such that a practical hatching rate is increased to not less than 98%.

In the present disclosure, the warm water includes preferably 0.1 g/L to 0.3 g/L of chitosan, 0.01 g/L to 0.2 g/L of hydroxypropyl cellulose and 0.05 g/L to 0.2 g/L of γ-aminobutyric acid, more preferably 0.15 g/L to 0.25 g/L of the chitosan, 0.05 g/L to 0.15 g/L of the hydroxypropyl cellulose and 0.1 g/L to 0.15 g/L of the γ-aminobutyric acid, and more preferably 0.2 g/L of the chitosan, 0.1 g/L of the hydroxypropyl cellulose and 0.1 g/L of the γ-aminobutyric acid. Adding the chitosan, the hydroxypropyl cellulose and the γ-aminobutyric acid to warm water improves a heat resistance of silkworm embryos, thus further improving the practical hatching rate.

In the present disclosure, an egg age of the silkworm eggs is preferably 17 h to 21 h, more preferably 18 h. The egg age is also a key factor affecting practical hatching rate. Experiments show that the silkworm eggs with an egg age of 17 h to 21 h have the practical hatching rate reaching not less than 98%, while an insufficient or excessive egg age reduces the practical hatching rate.

In the present disclosure, before immersion, a culture temperature of the silkworm eggs is preferably 24° C. to 26° C., more preferably 25° C. A culture humidity of the silkworm eggs is preferably 75% to 85%, more preferably 80%.

In the present disclosure, the silkworm eggs are also an important factor affecting hatching effect; the silkworm eggs are derived preferably from one or more varieties selected from a group consisting of 9 Fu, 7 Xiang, Liangguang 2, Yuecan 6 and Yuecan 8, with a hatching rate up to not less than 98%. Results of experiments on silkworm eggs derived from varieties such as Chuanshan×Shushui, An 3 and Gan 4 show that the Chuanshan×Shushui has a practical hatching rate of 86.37%, the An 3 has a practical hatching rate of 72.35%, and the Gan 4 has a practical hatching rate of 35.71%.

In the present disclosure, the silkworm eggs are preferably subjected to air-drying, incubation and hatching successively after the warm water immersion. The air-drying is conducted for preferably 20 min to 30 min, more preferably 25 min. The incubation or the hatching is conducted at preferably 26° C. to 28° C., more preferably 27° C. The incubation or the hatching is conducted at a relatively humidity of preferably 80% to 85%, more preferably 82%.

In the present disclosure, the silkworm eggs are treated using above hatching method, and cultured silkworm larvae can reach or even be superior to a level of the hydrochloric acid hatching method in terms of cocooning rate, whole cocoon weight, cocoon shell weight, cocoon shell rate and silkworm cocoon weight. It can be seen that hatching methods provided by the present disclosure can completely replace the hydrochloric acid hatching method, and has low cost, simple operation, and goes green, which is suitable for promotion and application of sericulture.

A warm water immersion-based hatching method of silkworm eggs provided by the present disclosure is described in detail below with reference to examples, but these examples may not be understood as limitation of a claimed scope of the present disclosure.

Example 1

After laying eggs, "Liangguang 2" silkworm eggs were placed at 25° C.±1° C. and a humidity of 80%±5% for protection; the silkworm eggs with egg ages of 11 h, 13 h, 15 h, 17 h, 19 h, 21 h and 23 h were placed in an aqueous solution (containing 0.2 g/L of chitosan, 0.1 g/L of hydroxypropyl cellulose and 0.1 g/L of γ-aminobutyric acid) and then treated at 50° C. for 15 s, followed by taking out and air-drying for 25 min; and the silkworm eggs were subjected to incubation and hatching, wherein 3 replicates were set for each treatment. A practical hatching rate was calculated according to formula I, and an egg age-practical hatching rate curve was drawn.

Practical hatching rate (%)=number of newly-hatched silkworms in two days/the total number of good eggs×100%   formula I Results were shown in FIG. 1. It could be seen from FIG. 1 that when an egg age was 17 h to 21 h, practical hatching rate reached not less than 98%, and could be up to 100%. However, the practical hatching rate was reduced at an insufficient or excessive egg age.

Example 2

After laying eggs, "Liangguang 2" silkworm eggs were placed at 25° C.±1° C. and a humidity of 80%±5% for protection; the silkworm eggs with an egg age of 17 h were placed in an aqueous solution (containing 0.2 g/L of chitosan, 0.1 g/L of hydroxypropyl cellulose and 0.1 g/L of γ-aminobutyric acid) for 15 s, wherein a temperature of warm water was set to 44° C., 46° C., 48° C., 50° C., 52° C. and 54° C. respectively, followed by taking out and air-drying for 25 min; and the silkworm eggs were subjected to incubation and hatching; and a practical hatching rate was calculated according to formula I, and an egg age-practical hatching rate curve was drawn.

Figure 2:
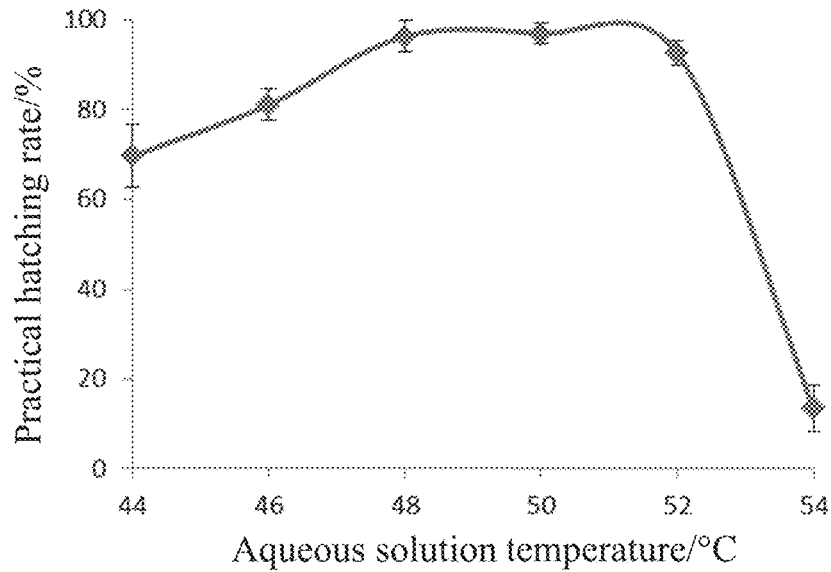
FIG. 2 shows an effect of a temperature of warm water on hatching rate of silkworm eggs of "Liangguang 2"

Results were shown in FIG. 2. It could be seen from FIG. 2 that when a water temperature is 48° C. to 51° C., a practical hatching rate reached not less than 98%, and could be up to 100%. However, the practical hatching rate was reduced at an insufficient or excessive water temperature.

Example 3

After laying eggs, "Liangguang 2" silkworm eggs were placed at 25° C.±1° C. and a humidity of 80%±5% for protection; the silkworm eggs with an egg age of 17 h were placed in an aqueous solution (containing 0.2 g/L of chitosan, 0.1 g/L of hydroxypropyl cellulose and 0.1 g/L of γ-aminobutyric acid) and then treated at 50° C. for 0 s, 5 s, 10 s, 15 s, 20 s, 25 s and 30 s, followed by taking out and air-drying for 25 min; and the silkworm eggs were subjected to incubation and hatching; and a practical hatching rate was calculated according to formula I, and an egg age-practical hatching rate curve was drawn.

Figure 3:
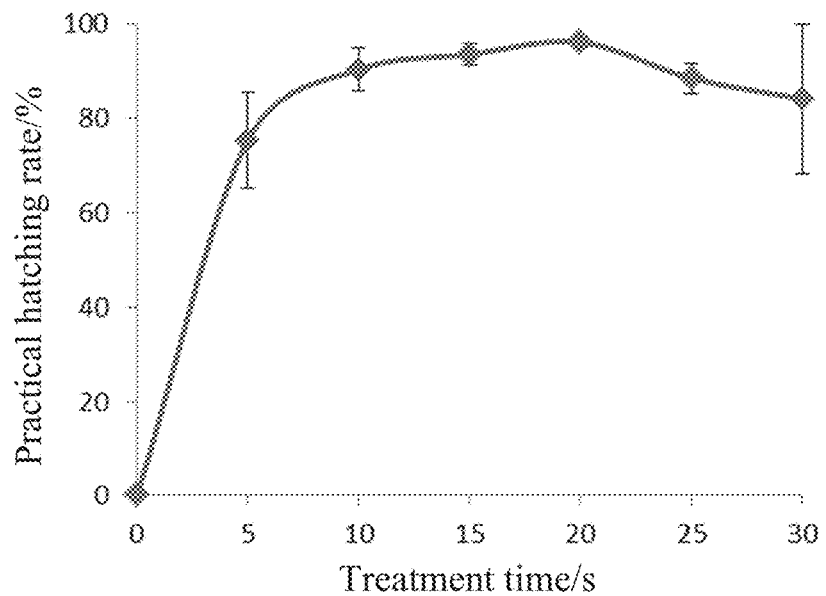
FIG. 3 shows an effect of a treatment time on hatching rate of silkworm eggs of "Liangguang 2"
Figure 4:
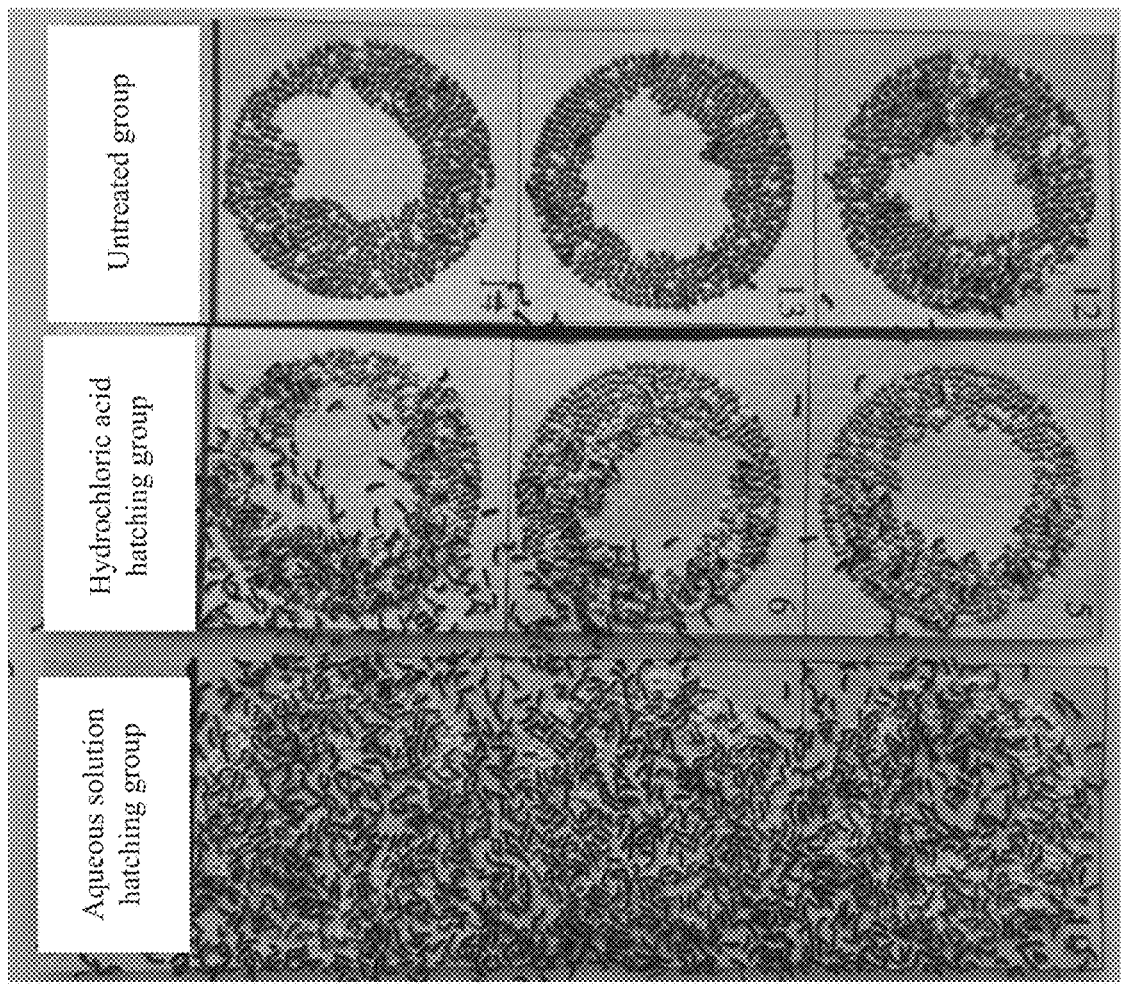
FIG. 4 shows hatching conditions of an untreated group, a hydrochloric acid hatching treatment group and an aqueous solution treatment group of silkworm eggs.

Results were shown in FIG. 3. It could be seen from FIG. 3 that when a treatment time is 15 s to 20 s, a practical hatching rate reached not less than 98%, and could be up to 100%. However, the practical hatching rate was reduced at an insufficient or excessive treatment time.

Example 4

An artificial hatching method of silkworm eggs included following steps:
17 h after laying eggs, silkworm eggs of a "Liangguang 2" quaternary hybrid were treated in a 50° C. aqueous solution (containing 0.1 g/L of chitosan, 0.2 g/L of hydroxypropyl cellulose and 0.05 g/L of γ-aminobutyric acid) for 20 s, followed by taking out for air-drying, incubation and hatching. A practical hatching rate reached 96.12%.

Comparative Example 1

A hydrochloric acid hatching-based artificial hatching method of silkworm eggs included following steps:
18 h after laying eggs, silkworm eggs of a "Liangguang 2" quaternary hybrid were treated in a hydrochloric acid solution (at a specific gravity of 1.075, 46° C.) for 5 min, followed by taking out for air-drying and incubation. A practical hatching rate was counted.

The hydrochloric acid hatching method had a hatching rate of 95.86%.

Example 5

An artificial hatching method of silkworm eggs included following steps:
18 h after laying eggs, silkworm eggs of a "Liangguang 2" quaternary hybrid were treated in a 51° C. warm aqueous solution (containing 0.2 g/L of chitosan, 0.1 g/L of hydroxypropyl cellulose and 0.1 g/L of γ-aminobutyric acid) for 15 s, followed by taking out for air-drying, incubation and hatching. Compared with a hydrochloric acid hatching method, an incubation time was shortened by 1 d, and a practical hatching rate reached 96.77%, which compared with Comparative Example 1 had no significant difference.

Example 6

An artificial hatching method of silkworm eggs included following steps:
20 h after laying eggs, silkworm eggs of a "Yuecan 8" quaternary hybrid were treated in a 50° C. warm aqueous solution (containing 0.3 g/L of chitosan, 0.05 g/L of hydroxypropyl cellulose and 0.1 g/L of γ-aminobutyric acid) for 20 s, followed by taking out for air-drying, incubation and hatching. A practical hatching rate reached 94.16%.

Example 7

An artificial hatching method of silkworm eggs, wherein a optimal treatment conditions were obtained through optimization of response surface experiment as follows: 18 h after laying eggs, silkworm eggs of a "Liangguang 2" quaternary hybrid were treated in a 50.5° C. warm aqueous solution (containing 0.2 g/L of chitosan, 0.1 g/L of hydroxypropyl cellulose and 0.1 g/L of γ-aminobutyric acid) for 15 s, followed by taking out for air-drying, incubation and hatching. A practical hatching rate was up to 98.48%.

Example 8

An artificial hatching method of silkworm eggs included following steps:
18 h after laying eggs, silkworm eggs of a "Liangguang 2" quaternary hybrid were treated in a 50° C. warm aqueous solution (containing 0.2 g/L of chitosan, 0.15 g/L of hydroxypropyl cellulose and 0.02 g/L of γ-aminobutyric acid) for 25 s, followed by taking out for air-drying, incubation and hatching. A practical hatching rate was up to 96.48%.

Example 9

An artificial hatching method of silkworm eggs included following steps:
18 h after laying eggs, silkworm eggs of a "7 Xiang" hybrid were treated in a 50.5° C. warm aqueous solution (containing 0.2 g/L of chitosan, 0.15 g/L of hydroxypropyl cellulose and 0.02 g/L of γ-aminobutyric acid) for 15 s, followed by taking out for air-drying, incubation and hatching. A practical hatching rate was up to 96.77%.

Example 10

18 h after laying eggs, silkworm eggs of a "Yuecan 6" hybrid were treated in a 50.5° C. warm aqueous solution (containing 0.2 g/L of chitosan, 0.15 g/L of hydroxypropyl cellulose and 0.02 g/L of γ-aminobutyric acid) for 15 s, followed by taking out for air-drying, incubation and hatching. A practical hatching rate was up to 97.82%.

Example 11

18 h after laying eggs, silkworm eggs of a "Liangguang 2" quaternary hybrid were treated in 50° C. pure water for 25 s, followed by taking out for air-drying, incubation and hatching. A practical hatching rate was 89.32%.

Comparative Example 2

18 h after laying eggs, silkworm eggs of a "Liangguang 2" quaternary hybrid were treated in a hydrochloric acid solution (at a specific gravity of 1.075, 46° C.) for 5 min, followed by taking out for air-drying, incubation and hatching. Statistics was conducted on cocooning rate, whole cocoon weight, cocoon shell weight, cocoon shell rate and 10,000-silkworm cocoon weight.

Example 12

An efficient artificial hatching method of silkworm eggs included following steps:
18 h after laying eggs, silkworm eggs of a "Liangguang 2" quaternary hybrid were treated in a 50° C. warm aqueous solution (containing 0.2 g/L of chitosan, 0.1 g/L of hydroxypropyl cellulose and 0.1 g/L of γ-aminobutyric acid) for 20 s, followed by taking out for air-drying, incubation and hatching. Statistics was conducted on cocooning rate, whole cocoon weight, cocoon shell weight, cocoon shell rate and 10,000-silkworm cocoon weight.

Statistical results of Comparative Example 2 and Example 12 are shown in Table 1.

TABLE 1

Feeding results of larvae after treating silkworm eggs by warm water hatching and hydrochloric acid hatching

| Source of silkworm eggs | Cocooning rate/% | Whole cocoon weight/g | Cocoon shell weight/g | Cocoon shell rate/% | 10,000-silkworm cocoon weight/kg |
|---|---|---|---|---|---|
| Experimental group | 97.52 | 1.36 | 0.26 | 19.00 | 13.32 |
| Control group | 96.27 | 1.35 | 0.26 | 19.42 | 13.05 |

As could be seen from data in Table 1, in terms of the cocooning rate, whole cocoon weight, cocoon shell weight, cocoon shell rate and 10,000-silkworm cocoon weight, there was no significant difference in a feeding effect of the warm water immersion-based hatching method provided by the present disclosure and the hydrochloric acid hatching method.

Example 13

An efficient artificial hatching method of silkworm eggs replacing the hydrochloric acid hatching method included following steps:

18 h after laying eggs, silkworm eggs of a "Liangguang 2" quaternary hybrid were treated in 50° C. warm water for 15 s, followed by taking out for air-drying, incubation and hatching. A practical hatching rate was calculated according to formula I.

A statistical method of a relative control effect was as follows:

Under normal conditions, "Liangguang 2" silkworms were raised with mulberry leaves until 5-instar newly hatched larvae were obtained, and Nosema bombycis ($10^5$/per silkworm) were fed to silkworm individuals through mulberry leaves during feeding. The silkworms were continued to be raised until mounting, and moths were ground for microscopic examination after moth emergence and egg production, and egg circles produced by moth with severe Nosema bombycis infection were selected for later use. Each infected egg ring (one brood) was divided into two parts, wherein one part was treated in an aqueous solution (egg age of 18 h, at 50° C. for 15 s), and the other part, as a control group, was treated according to the hydrochloric acid hatching method (at a specific gravity of 1.075, at 46° C. for 5 min). The silkworm eggs were raised normally after hatching, and microscopic examination was conducted on silkworms one by one after entering a 3rd-instar molting stage; an incidence of pebrine disease was counted according to whether N bombycis was present in the silkworm body, and a relative control effect was calculated according to formula II.

Relative control effect=(1−incidence rate of treatment group/incidence rate of control group)×100%   formula II A practical hatching rate was 94.23%, and warm water immersion-based hatching method had a relative control effect on silkworm pebrine disease of 86.66%.

Comparative Example 3

17 h after laying eggs, silkworm eggs of a "Chuanshan× Shushui", an "An 3" and a "Gan 4" were treated in 50° C. water for 20 s, followed by taking out for air-drying, incubation and hatching. A practical hatching rate was calculated according to the method of Example 1.

The "Chuanshan×Shushui" silkworm eggs had a practical hatching rate of 86.37%, the "An 3" silkworm eggs had a practical hatching rate of 72.35%, and the "Gan 4" silkworm eggs had a practical hatching rate of 35.71%.

Comparative Example 4

18 h after laying eggs, silkworm eggs of a "Liangguang 2" quaternary hybrid were treated as follows: in 59° C. warm water for 2 s, in 60° C. warm water for 1 s, in 59° C. warm water for 1 s, and in 58° C. warm water for 1 s respectively. Then the silkworm eggs were taken out for air-drying, incubation and hatching. A practical hatching rate was calculated according to formula I.

After short-term immersion of "Liangguang 2" silkworm eggs in warm water of different temperatures, obtained practical hatching rate results were shown in Table 2.

TABLE 2

Effects of short-term immersion in warm water at different temperatures on hatching

| Treatment group | Practical hatching rate |
|---|---|
| 59° C. warm water for 2 s | 75.21% |
| 60° C. warm water for 1 s | 75.82% |
| 59° C. warm water for 1 s | 76.04% |
| 58° C. warm water for 1 s | 74.69% |

It could be seen that shortening immersion time while increasing temperature of warm water did not have a favorable effect on hatching effect of silkworm eggs, but reduced a practical hatching rate.

The above descriptions are merely preferred embodiments of the present disclosure. It should be noted that a person of ordinary skill in the art can further make several improvements and modifications without departing from the principle of the present disclosure, but such improvements and modifications should be deemed as falling within the claimed scope of the present disclosure.

What is claimed is:

1. A warm water immersion-based hatching method of silkworm eggs, comprising following steps:
   subjecting the silkworm eggs to warm water immersion at 49° C. to 51° C. for 15 s to 23 s;
   wherein the warm water comprises 0.1 g/L to 0.3 g/L of chitosan, 0.01 g/L to 0.2 g/L of hydroxypropyl cellulose and 0.05 g/L to 0.2 g/L of γ-aminobutyric acid.

2. The warm water immersion-based hatching method of silkworm eggs according to claim 1, wherein the warm water comprises 0.15 g/L to 0.25 g/L of the chitosan, 0.05 g/L to 0.15 g/L of the hydroxypropyl cellulose and 0.1 g/L to 0.15 g/L of the γ-aminobutyric acid.

3. The warm water immersion-based hatching method of silkworm eggs according to claim 1, wherein a temperature of the warm water immersion is 50.5° C., and a time of the warm water immersion is 15 s.

4. The warm water immersion-based hatching method of silkworm eggs according to claim 1, wherein an egg age of the silkworm eggs is 17 h to 21 h.

5. The warm water immersion-based hatching method of silkworm eggs according to claim 4, wherein the egg age of the silkworm eggs is 18 h.

6. The warm water immersion-based hatching method of silkworm eggs according to claim 1, wherein before the warm water immersion, a culture temperature of the silkworm eggs is 24° C. to 26° C. and a culture humidity is 75% to 85%.

7. The warm water immersion-based hatching method of silkworm eggs according to claim 1, wherein the silkworm eggs are derived from one or more varieties selected from a group consisting of nine Fu, seven Xiang, Liangguang two, Yuecan six and Yuecan eight.

8. The warm water immersion-based hatching method of silkworm eggs according to claim 7, wherein the silkworm eggs are subjected to air-drying, incubation and hatching successively after the warm water immersion.

9. The warm water immersion-based hatching method of silkworm eggs according to claim 8, wherein the incubation or the hatching is conducted at 26° C. to 28° C. and a relative humidity of 80% to 85%.

10. The warm water immersion-based hatching method of silkworm eggs according to claim 7, wherein the warm water comprises 0.1 g/L to 0.3 g/L of chitosan, 0.01 g/L to 0.2 g/L of hydroxypropyl cellulose and 0.05 g/L to 0.2 g/L of γ-aminobutyric acid.

11. The warm water immersion-based hatching method of silkworm eggs according to claim 7, wherein the warm water comprises 0.15 g/L to 0.25 g/L of the chitosan, 0.05 g/L to 0.15 g/L of the hydroxypropyl cellulose and 0.1 g/L to 0.15 g/L of the γ-aminobutyric acid.

12. The warm water immersion-based hatching method of silkworm eggs according to claim 7, wherein a temperature of the warm water immersion is 50.5° C., and a time of the warm water immersion is 15 s.

13. The warm water immersion-based hatching method of silkworm eggs according to claim 7, wherein an egg age of the silkworm eggs is 17 h to 21 h.

14. The warm water immersion-based hatching method of silkworm eggs according to claim 7, wherein an egg age of the silkworm eggs is 18 h.

15. The warm water immersion-based hatching method of silkworm eggs according to claim 7, wherein before the warm water immersion, a culture temperature of the silkworm eggs is 24° C. to 26° C. and a culture humidity is 75% to 85%.

\* \* \* \* \*